United States Patent
Hauge

(10) Patent No.: US 9,335,315 B2
(45) Date of Patent: May 10, 2016

(54) WETLAND METER

(71) Applicant: Odd Hauge, Kirkland, WA (US)

(72) Inventor: Odd Hauge, Kirkland, WA (US)

(*) Notice: Subject to any disclaimer, the term of this patent is extended or adjusted under 35 U.S.C. 154(b) by 308 days.

(21) Appl. No.: 13/936,052

(22) Filed: Jul. 5, 2013

(65) Prior Publication Data

US 2014/0157888 A1   Jun. 12, 2014

Related U.S. Application Data

(60) Provisional application No. 61/668,322, filed on Jul. 5, 2012.

(51) Int. Cl.
*G01F 23/00* (2006.01)
*G01N 33/24* (2006.01)

(52) U.S. Cl.
CPC .................... *G01N 33/246* (2013.01)

(58) Field of Classification Search
CPC .................................................. G01N 33/246
USPC .......... 73/73, 152.18, 152.39, 152.41, 290 R; 137/78.3
See application file for complete search history.

(56) References Cited

U.S. PATENT DOCUMENTS

| | | | | |
|---|---|---|---|---|
| 3,910,300 | A * | 10/1975 | Tal | 137/78.3 |
| 5,941,121 | A * | 8/1999 | Faybishenko | 73/73 |
| 6,263,726 | B1 * | 7/2001 | Hubbell et al. | 73/73 |
| 6,308,563 | B1 * | 10/2001 | Hubbell et al. | 73/152.51 |
| 6,823,264 | B1 * | 11/2004 | Hauge | 702/6 |
| 7,107,151 | B2 * | 9/2006 | Hauge | 702/1 |
| 2009/0038390 | A1 * | 2/2009 | Dahan | 73/152.24 |
| 2013/0080074 | A1 * | 3/2013 | Farsad et al. | 702/25 |

OTHER PUBLICATIONS

"Corps of Engineers: Wetlands Delineation Manual," Technical Report Y-87-1, Environmental Laboratory, U.S. Army Corps of Engineers, Jan. 1987, 143 pages.
Gillham, R.W., "The Capillary Fringe and Its Effect on Water-Table Response," Journal of Hydrology 67(1-4):307-324, Jan. 1984.
Hooghoudt, S.B., "Waarnemingen van Grondwaterstanden voor de Landbouw," Commissie voor Hydrologisch Onderzoek TNO, Verslagen Technische. Bijeenkomsten 1-6:185-201, 1947.

* cited by examiner

*Primary Examiner* — Hezron E Williams
*Assistant Examiner* — Hoang Nguyen
(74) *Attorney, Agent, or Firm* — Christensen O'Connor Johnson Kindness PLLC

(57) ABSTRACT

A system (100) for measuring the depth of saturated soil includes a water level detector (102) along with a stimulating/actuating device (104) that directs an actuating medium into the ground at the elevation of the capillary fringe or below the elevation of the capillary fringe. The actuating medium may consist of water, ultrasound emissions, or vibrations.

22 Claims, 2 Drawing Sheets

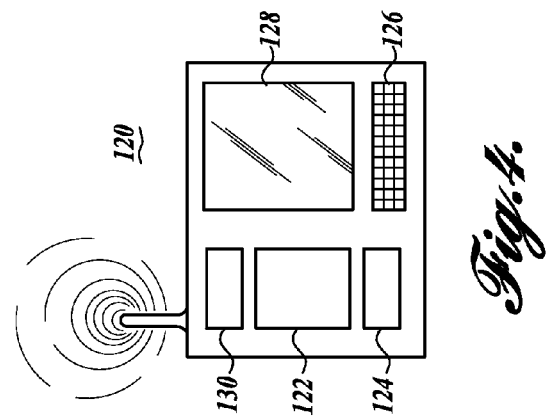
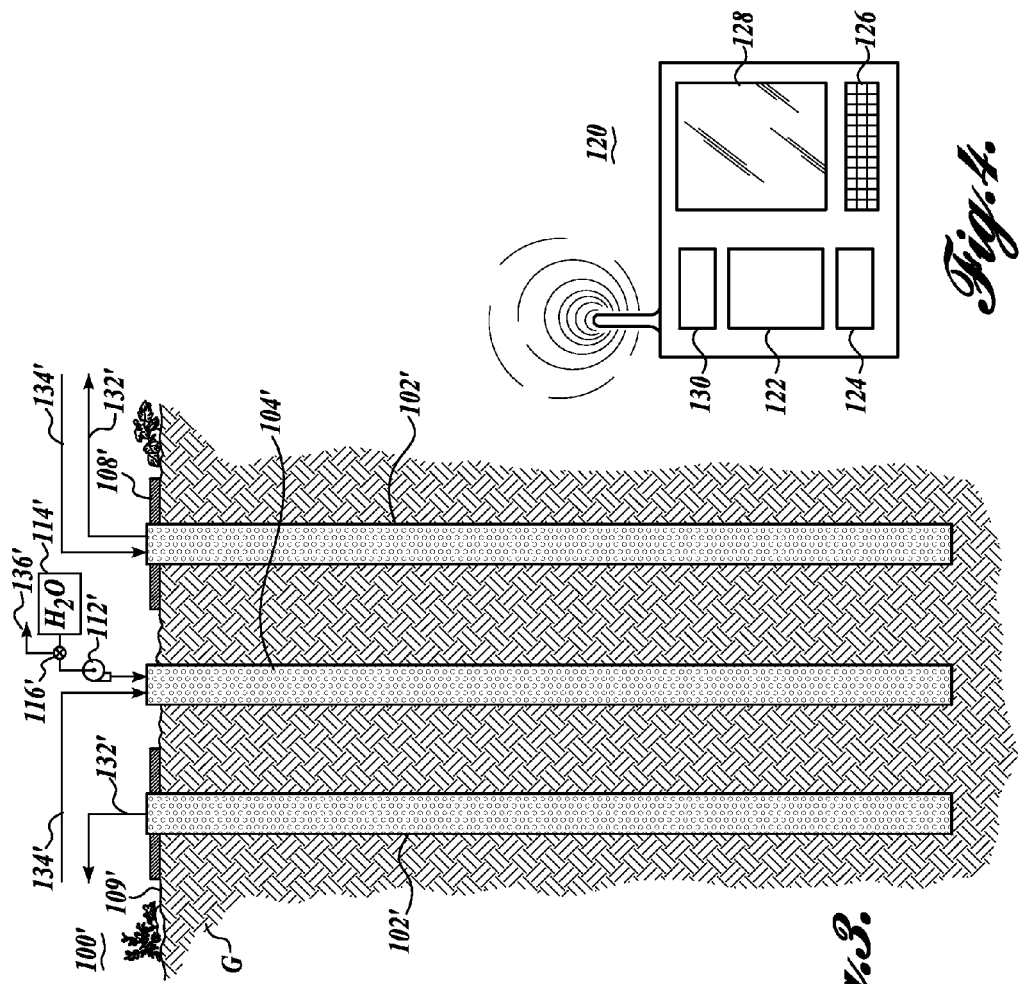
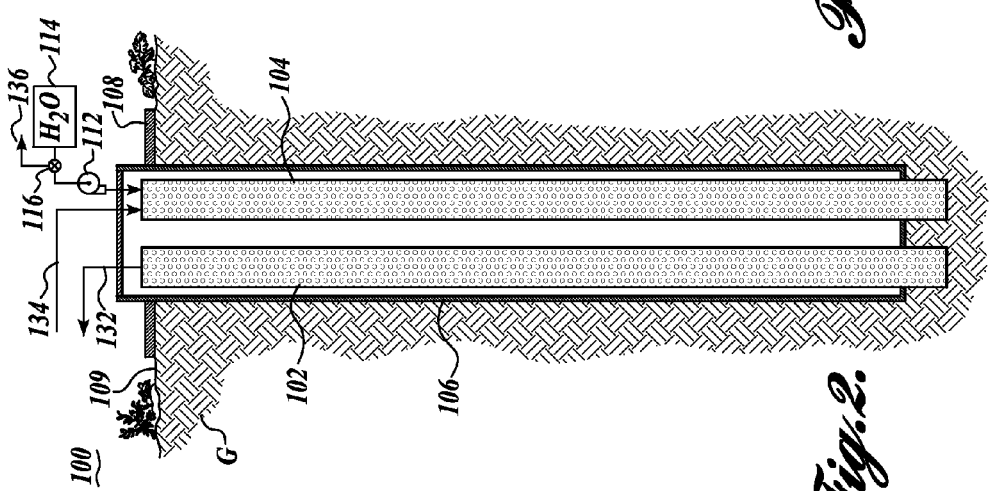

WETLAND METER

CROSS-REFERENCE TO RELATED APPLICATION

The present application claims the benefit of U.S. Provisional Application No. 61/668,322, filed Jul. 5, 2012, the disclosure of which is incorporated by reference herein.

FIELD OF THE INVENTION

The invention relates to systems and methods of determining the depth to saturated soils and more particularly to using that information to determine whether a particular site is a wetland.

BACKGROUND

Wetlands may include marshes, bogs, and swamps. Wetland delineations tend to be controversial because such a determination often pits the interest of environmentalists against the interests of landowners and/or land developers. Therefore, standards or guidelines have been created to standardize wetland delineations. These guidelines also attempt to balance the interests of the public and private landowner/developer. According to typical guidelines, whether a particular parcel of land qualifies as a wetland generally depends upon the percentage of the growing season that the surface of the soil is continuously saturated with water.

One example of wetland delineation guidelines includes the Corps of Engineers' Wetlands Delineation Manual of January 1987 ("'87 Manual"). The '87 Manual provides guidelines that may be used to determine whether a particular parcel of land is a wetland. Generally, land qualifies as a wetland if it is continuously saturated to the surface between 5% and 12.5% of the growing season. However, the '87 Manual indicates that many sites are not wetlands despite being continuously saturated to the surface between 5% and 12.5% of the growing season. Delineation in these cases is left to the judgment of the delineator (person who determines whether a site is a wetland). According to the '87 Manual, sites not continuously saturated at least 5% of the growing season are not wet enough to be considered wetlands.

The '87 Manual provides that delineators may consider three parameters, soil characteristics, vegetation, and hydrology, when evaluating whether a site is a wetland. Soil characteristics may be used to determine whether the soils at the site are hydric soils. Hydric soils form under conditions of saturation, including flooding that persists long enough to develop anaerobic conditions in the soil. These anaerobic conditions, characteristic of hydric soils, may be observed as color changes in the soils.

Direct determination of the hydrological parameter is difficult. Capillary forces pull the water table down below the level of soil saturation. The '87 Manual defines wetland according to variations in "depth to saturated soils" during the growing season. Depth to saturated soils can only be measured directly when the effect of capillary forces are momentarily cancelled. This happens at the onset of rain or when an artificial stimulus is provided.

Wetland determination becomes controversial when a delineator relies mainly on vegetation and soil characteristics to assess how the hydraulic parameter depth to saturated soils varies during the growing season. Accurately evaluating the site according to its hydrology requires numerous visits. However, it is not uncommon for a delineator to make a determination based on only a single visit.

Digging a pit in the ground and measuring the depth at which water appears in the pit will yield the depth of the water table (the upper boundary of a free groundwater body at atmospheric pressure). However, the depth of the upper boundary of saturated soil (referred to hereafter as the depth to the saturated soil) is not necessarily equal to the depth of the water table. Capillary action may draw water up through the grains of soil to a level above the water table causing saturated soil to occur above the water table. (See FIG. 1A.) The volume of water located between the depth to the saturated soil and the water table is known as the capillary fringe. Both the depth to the saturated soil and the water table may rise during rainfall and shrink when depletion mechanisms such as drainage, evaporation, and transpiration deplete water from the soil.

The capillary fringe is, in essence, a zone of negative pressure that extends from the saturation level down to the water table. As shown in FIG. 1A, the pressure differentials across membrane spans, such as "a" and "b," balance each other out. The spans are taut, there is no flow, and there is a negative pressure zone. The mechanics of capillary actions that creates the capillary fringe are discussed in applicant's corresponding provisional patent application, No. 61/668,322, incorporated herein by reference.

The following also provides an explanation of the mechanics of capillary actions that applicant believes is applicable to the creation of the capillary fringe:

1. Introduction to Capillary Mechanics

The reverse-Wieringermeer effect, reported by Hooghoudt (*Waarnemingen van grondwaterstand voor de landbouw*, Commissie voor Hydrologisch TNO, Verslagen Technische. Bijeenkomsten 1-6; 185-201 (1947)), is an enigma, tensile strength in water counter-intuitive, and the concept of "surface tension" does not help in the investigation of either one. The mysteries nest within each other like Matryoshka dolls. To explain the reverse-Wieringermeer effect, it is necessary to "visualize" the capillary mechanism, which in turn requires understanding that water has tensile strength. Also, some simplifying assumptions are required.

Stensrud (Simen Stensrud, lecture (Ila Elementary School)), ca. 1944) visualized that water molecules all "hold hands" with their neighbors, but those at the surface have no one on the outside to hold hands with so they double up on the grip with their extra hands, which causes "surface tension."

As the scale is reduced from macroscopic to microscopic, "mechanics-as-we-know-it" "warps" to "capillary mechanics." The generally accepted mathematics (ref. for instance, Dingman (S. Lawrence Dingman: Physical Hydrology, $2^{nd}$ ed., Prentice Hall)), (eq. B5) does not warp along with the real world as the former contains a singularity. 'Surface tension' is misleading; there is tension everywhere in a body of water at the same time that there is compression, i.e. water is pre-stressed—and not just at the surface. "Tension" in water must reach the tensile strength before a molecule can be pulled away. A number of pitfalls are bypassed by not looking directly at the tension imposed by adhesive forces near a line of contact, but at the remainder when it is subtracted from the pre-tension that exist everywhere in liquid water.

The "stand-in" water molecule is made up from subassemblies, which are in turn made up from sub-subassemblies, etc., in the manner of "real-world" molecules. The polarity, and other inconvenient characteristics not important for visualization, can be "stripped away" from the actual molecule.

Attractive forces pull molecules toward each other until they are one "diameter" apart. A growing repulsion keeps them from getting closer to each other. The molecules "levitate" off one another in a "no-touch" situation similar to when centrifugal forces "levitate" the Moon off the Earth. The molecules "cohere" and pre-tensions water; it is in tension and compression at the same time, and the pre-tension must be overcome before a molecule can be separated from a body of water.

In liquid water, molecules slip around each other with ease and reduce the potential energy of the attractive forces. An unconfined body of water assumes a spherical shape where the energy is least. If a "body of water" consists of three molecules, all touching each other, the energy per molecule required to rip one loose from another and swing it around and line them up in a row is relatively large. The energy requirement per molecule, in order to make and break bonds and move them around without stripping them away from the main body becomes progressively less in larger and larger bodies.

Cohesion dominates the "sphere-forming effort" in drops; however, it is a local phenomenon, and as a body of water grows in size, it "loses firmness." A golf-ball sized body can be generated with some difficulty in a "gravitation-free" environment, but the cohesive forces can barely hold it together. In contrast to gravitational forces, cohesive forces do not 'accumulate' to a noticeable extent.

Gravity attracts everything to everything else but the force is so weak that it does nothing to hold small bodies of water together. A cumulative effect only becomes prominent in large bodies of water.

The attractive forces between glass and water are stronger than between water and water. Water "adheres" to glass but if the adhesive forces equaled the intermolecular forces, the angle of contact would be 90-degrees instead of zero.

Raindrops and planet-size bodies of water are free (self-contained) and 'separate' when no external forces interfere with cohesion and gravity. But soil particles, which are assumed to be made of glass, partially confine water in the interstices. At the air-water interface, adhesive forces at the lines of contact drag water along the confining solids.

Tight spaces "warps mechanics into capillary mechanics" and gives rise to the reverse-Wieringermeer effect—which Einstein (Albert Einstein: *Folerungen aus den Capillarität-serscheinungen*, Annalen der Physik, 4 (513-523)) had not heard of when he published his first paper in 1901. Einstein brought other substances than glass, water, and air to the table.

2. Pre-Stresses in Liquid Water

If "theoretical tweezers" lift one water molecule at the surface in a glass of water up, other molecules will hang on below due to cohesion. In turn, more and more hang on until the weight of water snaps the bonds at the upper molecule where water reaches its tensile strength.

Because molecules have dimensions, the lifting force on the upper molecule, represented by an arrow, must be the resultant of a distributed force. The cohesive forces that bond the upper molecule to the next ones down are also resultants of distributed forces. The arrows in a typical vector diagram do not reflect this, which means that the theoretical stress, in terms of force per unit area, is infinite and the mathematics reflects a singularity. An improved model of how forces work on matter at the molecular level is needed so that equations can be written to apply to this situation.

Before water molecules can be separated from one another, they slip around and the force to lift one molecule from a surface spreads out over more and more molecules and the stress at the 'hangers-on' diminishes rapidly.

In a glass of water, a "meniscus" is visible at the wall. The stress at the line of contact, where the meniscus surface intersects the wall, must equal the "bulk tensile strength of water" if the angle of contact is zero. For a mathematical surface, where the stress is zero, the water table, is not far below.

To visualize "tension" in water, it is best to look at what remains after it has been subtracted from the pre-tension that exists everywhere in liquid water. At the line of contact, it is zero and at the water table, pre-tension remains. The force-field lines of this "differential tension" converge and meet at the line of contact where the 'tension' reaches the "tensile strength" of water, which means that the molecules are ripped away from one another.

By subtracting "tension" from pre-tension, the "uncertainties" at the line of contact are stripped away, but only there. Near the line of contact, but not at it, the two forces are not equal. To what extent they grow different further away is uncertain except it does not matter for purposes of this analysis. There are uncertainties regarding how "Fermions" (matter particles) and 'Bosons' (force particles) interact at the molecular level but the problem belongs to the physicists and rather than to consult with them, one uncertainty is subtracted from another and it is assumed that they are equal at the line of contact. That makes the differential zero at the line of contact. With that, the math challenge becomes trivial.

All uncertainties are lumped into one by saying that somewhere near the line of contact the "tension" equals the "bulk tensile strength" of water. In order to explain the reverse-Wieringermeer effect, it is not necessary to know about the "polarity" of water molecules, and so on. In a capillary tube, the up-forces near the line of contact divided by the cross sectional area of the tube yields stress; it is a negative pressure that lifts water up to a height that is inversely proportional to the tube diameter.

It is "inversely proportional" if working with "surface tension" as well, but then one may lose sight of the tension that exists elsewhere. The spacing between the equipotential lines of the "remainder" after tension is subtracted from pre-tension, is zero at the line of contact, and widen towards the water table where the tension is equal to the pre-tension in the water.

3. The Capillary Effect

The geometry of the air-water interface curvature resembles an "Euler spiral" more than a meniscus; the tension in the water is high where the radius of the curvature is small and approaches zero if and when the interface "flattens out." In a glass of water, the "flat portion" of the interface coincides with the water table. But where the air-water interface begins to curve upward, the water table extends to the wall. Whether the water table is entirely flat or not is not of consequence here.

A capillary tube has a small diameter and the curvature of the air-water interface does not "flatten out," it "turns around and goes back up on the other side." Instead of "petering out" towards the water table, the tension only dilutes from the line of contact to the nadir of the curvature where it is still negative. Confined by glass, the tension in the water continues down the tube from the nadir of the air-water interface to the water table. Capillary action results when the forces at a line of contact do not dilute entirely before the air-water interface 'turns around and goes back up the other side' due to the confinement of a "capillary space."

It is not necessary to know the exact tensile strength of water in order to calculate that the rise of water in a capillary tube is inversely proportional to the diameter. In that case, it is necessary to know the "diameter" of the molecules and how the 'tension' varies across their "diameters". However, exact values are not needed as long as the analysis is limited to saying that the 'remainder-tension' is zero at the line of contact and at the 'pre-tension level' at the water table.

4. Separate Bodies of Water

Liquid water only exists as "separate bodies," they can be confined, partially confined, unconfined—i.e. self-contained. A self-contained body of water assumes a spherical shape when no external forces work on it. If water is confined, the pressure goes up everywhere if a single molecule is added; the "communication" within one and the same body is flawless.

No stress information is exchanged between the seven seas and a small drop of water hovering just above the surface because they are separate bodies. Drops forming at a leaking faucet are part of a body of water that extends down through the plumbing from "a lake somewhere," until they gain weight and snap off. If a faucet is carefully opened so there is a glass-smooth jet coming out, it is possible to see how cohesive forces fight gravity. The "specimen" necks down as gravity accelerates it while cohesive forces "grow drops." They break loose and momentarily the "tip of the jet" is "pointy," but new drops soon form.

5. The Reverse-Wieringermeer Effect

Water table measurements taken over a nine month time period (1997-1998) by the applicant, about 4000 in all, showed that the water table can move up much farther and faster at the onset of rain than expected from the water input. An explanation of the phenomenon is provided in an article by Gillham (*The Capillary Fringe and its Effect on Water-Table Response*, Journal of Hydrology, 67 (1984) 307-324 S.B.). Gillham found that the application of 3 mm of water to the soil surface on a test site shifted the water table about 300 mm in less than 15 seconds. Hooghoudt (see Section 1 above) had noted this (1947) and labeled it the "reverse-Wieringermeer effect."

6. Spans

Air-water interfaces stretch or "span" between lines of contact. If the spans are short, like in capillary tubes, stress concentrations in the water near the lines of contact do not fully dissipate by mid-span; a negative stress or pressure continues from there down the tube until it reaches zero at the water table where it turns positive. As spans get shorter, stresses increase in inverse proportion to span length.

7. Water Between Marbles

A small amount of water between two marbles will stay tenaciously in place when the marbles are moved around. The water necks down and snaps like a "test specimen" when the marbles are pulled apart. There are two lines of contact and a single span stretching between them.

The water bonds marbles, although with "shooting" size ones the "bonding forces," are hardly noticeable. If a number of marbles are assembled and bonded with small amounts of water, the "construction" has little "structural strength." However, the negative pressure at each span is inversely proportional to its length, and the "tensile strength" of the whole "structure" ends up increasing in inverse proportion to the marble diameters.

High stresses, or negative pressures, reduce evaporation rates. If spans are short, water may not evaporate. Aside from a molecular layer of water adhering to them, soil particles tend to be dry between lines of contact. The stresses in partially-confined water in soil-particle interstices are not affected by this.

8. Scale-Related Warp

If three (vertical) glass rods are clamped together like a bundle of straws with one end stuck in a dish of water, they constitute a "tube" (with a non-circular hole) and a top view of the construction will look like "three coins, all touching, laid out on the table." If the rod diameters are as large as those of pennies, there will be no visible "capillary action" except small menisci near the lines of contact.

If the scale is reduced, water will start to rise between the rods. Adhesive and cohesive forces overcome gravity in "capillary" spaces as the scale goes from "macro" to "microscopic".

At small scales, the rods can even be spaced a "capillary distance" apart. If the "coins-on-the-table" are spaced a "coin-thickness" apart they form a "leaky" tube. However, a cross section taken half-way up the column of water in small-scale "leaky tubes," shows that instead of leaking out the water stays in place. The three convex air-water surface spans reflect a stress in the water behind them that controls their movement, while the spans are biased to move outward, they lose "strength" relative to another as they move because other spans must shorten when the volume of water is constant.

From top to bottom, the air-water-interface spans in the leaky tube are as short as they can be near the top, where they draw the highest negative pressure in the water. Toward the bottom, the spans get longer until there is no negative pressure behind them at the water table. There, the effort of gravity equals the combined efforts of adhesion and cohesion; the resulting stress or pressure is zero, and the water "leaks" out.

A paper towel is a "leaky" structure that "wicks" water up to a height of maybe 10-inches. The pressure is, maybe, negative 10-inch of water at the top and zero at the water table.

9. Water Between Two Flat Plates

In order to determine the "bulk tensile-strength of water," consider two circular, flat plates. Place a small amount of water between them. Keep the plates parallel and centered while pulling them apart. The negative pressure in the water varies in inverse proportion to the span length—the distance between the plates.

With flat plates, little water and short spans, the stress is as high as it can get. The stress at the nadir of the air-water interface curvature continues throughout the body of water and we can calculate it at the time the bonds break. This would be close to the "bulk tensile strength of water" while the "theoretical stresses" near a line of contact would be higher.

10. Air-Water Interfaces in Soils, Fronts

Consider the air-water interface in a bucket of potatoes half filled with water. It resembles a perforated plate with part of a potato stuck in each hole, or perhaps the map of a lake with islands, some poking out of the water from below and others dipping into the water from above. The outlines of the islands are "lines of contact".

Next, visualize soil as small glass particles of random size and shape. Forces at the lines of contact will try to move the spans in the "perforated plate"—the air-water interface—until the pressure mid-span everywhere is the same. The spans sag like "hammocks" in reaction to negative pressures between lines of contact as the air-water interface adjusts in order to equalize pressure.

The spans between the particles lengthen and shorten as the air-water interface propels itself down the interstices. A front at the air-water interface seeks an equilibrium position where any span that lengthens when it tries to move forward will be held back by spans that shorten in response.

Air-water interfaces in soils are "fronts," some are "open" and others "closed." A closed front encloses a body of water while an open front does not. Opposing spans are mostly responsible for negative pressures in enclosed bodies while the weight of water determines the negative pressure below open fronts.

11. Moisture

The water within a closed front is a separate body of water. Moisture can be regarded as small bodies of water within closed fronts. As a front moves toward an equilibrium position, the water may subdivide. Evaporation reduces both volumes and pressures of bodies of water. The pressure may go so low that plants cannot access it.

12. Ground Water

Ground water is commonly considered to be water below the water table, i.e. water under positive pressure. However, open fronts at the air-water interface pull the water table down in dry weather when there is no water input. Meanwhile, the saturation level stays where it is. Lest there be two groundwater levels, it is considered that the level revealed by the water table at the onset of rain is the "proper" one.

The negative pressure at a front pulls the water table down, creating a negative-pressure zone or capillary fringe. However, a front is refractory; the first drop of water to merge with it at the onset of rain cancels the negative pressure near the point of intrusion. The water table moves up quickly, 300 mm in 15 seconds as Gillham (5) measured it. That is too quickly to consider flow; the water is already there and the water table merely shifts within it.

As more water follows, the situation becomes chaotic and remains so until the water input stops so that the air-water interface spans can "close ranks" and pull the water table back down. Data from 1997-1998 indicate that it takes longer to re-establish a capillary fringe than the 15 seconds or so that is needed to destroy it.

13. Miscellaneous Water-Related Phenomena

While the air-water interface in a capillary tube is enclosed within a circle; in a soil it is excluded from areas that lie within lines of contact. The propulsive power is still proportional to the cosine of the angle of contact except the surface geometry is no longer that of a cylinder but of a variety of objects, including soil grains, rocks, roots, and voids.

Whether a front exists in a tube or in a soil, span length is essential. In a tube, the air-water interface at the front spans the length of the diameter. In a soil, there are many spans of various lengths that keep adjusting as the front moves toward a position and the pressure behind all find a position where the forces balance. The spans sag under stress, and the negative pressures must be the same at mid-span everywhere when the elevation above the water table is counted in and the water doesn't flow.

Adhesive forces draw water towards the void in pits, like those dug to investigate water levels, but they run out of soil grains to latch onto before they get there. A front stops as it nears the wall, dropping from the saturation level, to the water table, where it crosses over before rising back up along the opposite wall. No visible "ring" reveals "depth to saturated soils", as the '87-Manual (U.S. Army Corps of Engineers: *Wetlands Delineation Manual*, Technical Report Y-87-1 (January 1987)) calls it. The capillary fringe hangs with its whole weight from soil particles at the saturation level, and the reaction forces from the weight of water transmit downward and "compress" soil particles.

Sand consists of relatively large particles. Water under negative pressure lends some structural strength but that diminishes as it evaporates. Sand castles collapse when they dry out. Saturating water under positive pressure pushes the walls into the pits when digging for clams and it pushes the lower parts of sand banks out while negative pressures higher up lend structural stability there. The angle of repose varies with water content.

Soils have smaller particle sizes than sand, and water that remains locked up in lumps of dry soils gives them structural strength until they are crushed. The water quickly evaporates and there should be a small, but measurable, weight difference between a lump and the dust that is left after it has been crushed.

Particle size and shape play a role in determining whether or not large closed fronts exist in clays. "Quick clays" are saturated with water within closed fronts where short spans keep it from evaporating. Reaction forces clamp the particles together as if the air was pumped out of a rubber bag full of sand. Momentarily disturbing the front with a hard blow cancels the low pressure within. Visible water, liquefaction, may show up in pottery clays and landslides.

A piece of paper placed on top of potatoes in a bucket contacts them at points. The air-water interface of a drop of water that rests on a dry soil deforms so that the lines of contact will not be at points but they enclose "areas." While the air-water interface in a capillary tube is enclosed within a circle; the air-water interface of a drop has areas that are excluded from it, like the holes in a perforated plate. Forces at the lines of contact that outline the excluded areas, assisted by the weight of water, draw water toward the interstices while cohesive forces try to keep the water from deforming. Unless there is sufficient moisture present, the pressure at the contact area due to gravity is too small to overcome the cohesive forces and the water "beads up" on top.

14. Terminology

Capillary Fringe: Water under negative pressure between the saturation level and the water table.

Front: The air-water interface (surface) in a soil; capillary forces bias it to move.

Depth to Saturated Soils: The vertical distance from the surface to the saturation level.

Ground Water: Water below the water table, water under positive pressure.

Moisture: Isolated bodies of water in the soil, generally above the saturation level.

Negative-Pressure Zone: The capillary fringe.

Reverse-Wieringermeer Effect: The rapid shift of the water table to the saturation level at the onset of rain.

Saturated Soils: A soil is saturated when the interstices between soil grains are completely filled with water.

Saturation Level The level below which a soil is saturated.

Single Spans: Bodies of water lodged between two glass beads or marbles have single spans.

Span: The distance between lines of contact at the air-water interface.

Water Table: A surface at atmospheric pressure. It shows up physically in a dug hole or a well.

The capillary fringe makes it difficult to accurately determine the saturation level. The present application provides systems and methods for temporarily eliminating the negative pressure zone by disturbing the existing pressure differential at the saturation level. As a consequence, while the capillary fringe is temporarily collapsed, the water table moves up to the saturation level. This is illustrated in FIG. 1B.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A system is disclosed for measuring the depth to saturated soil includes a water level detector capable of measuring the distance from the ground surface to the water table, as well as a stimulating device to direct an actuating medium into the ground at the elevation of the capillary fringe or below the elevation of the capillary fringe, which has the effect of temporarily eliminating the capillary fringe adjacent the stimulating device. Also, a recording device is used to record the measurements of the water level detector.

In accordance with a further aspect of the present disclosure, the water level detector may include a piezometer or a tensiometer.

In accordance with a further aspect of the present disclosure, the stimulating device may be of various configurations. In one configuration, the stimulating device may be configured to direct water into the ground adjacent the stimulating device at an elevation corresponding to the capillary fringe, or above or below it in elevation. The water used for this purposes may originate from the ground water adjacent the stimulating device, or may be provided from an external source.

Other forms of the stimulating device may include an ultrasound frequency emitter to emit ultrasound frequencies into the capillary fringe or just below the capillary fringe. The stimulating device may, in a different form, include a vibration generator to impart vibrations into the capillary fringe or at an elevation just below the capillary fringe.

The system of the present disclosure may also include a control system to control the operation of the stimulating device, as well as the operation of the water level detector. The control system can further control the recording of the output of the water level detector. The control system may be located at the site of the stimulating device and water level detector. Alternatively, the control system may be remotely located, and wirelessly communicate with the stimulating device and water level detector.

In accordance with the present disclosure, a method is provided for measuring depth to saturated soil, including temporarily collapsing the capillary fringe by imparting an activating medium into the soil at or below the elevation of the capillary fringe. Thereupon, or closely thereafter, the method includes measuring the depth to saturated soil at the location of the collapsed capillary fringe.

In accordance with the method of the present disclosure, the activating medium introduced into the soil may include water in sufficient quantities to collapse the capillary fringe. Such water may consist of collected adjacent ground water or water from a remote location.

In a further aspect of the present method, the activating medium may consist of ultrasonic emitters or vibration generators to emit ultrasonic radiation or vibrations at or below the elevation of the capillary fringe.

In accordance with the method of the present disclosure, the depth of saturated soil can be measured using piezometer or a tensiometer, or other types of comparable instruments. The measurements from the instrument utilized can be transmitted to a remote location for monitoring, recording, analysis, etc.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a schematic elevational view of a wetland meter system of the present disclosure;

FIG. 3 is a further embodiment of the present disclosure of a wetland meter system; and FIG. 4 is a schematic view of a remotely located control system for controlling the wetland meter systems of FIGS. 2 and 3.

DETAILED DESCRIPTION

Figure 1A:
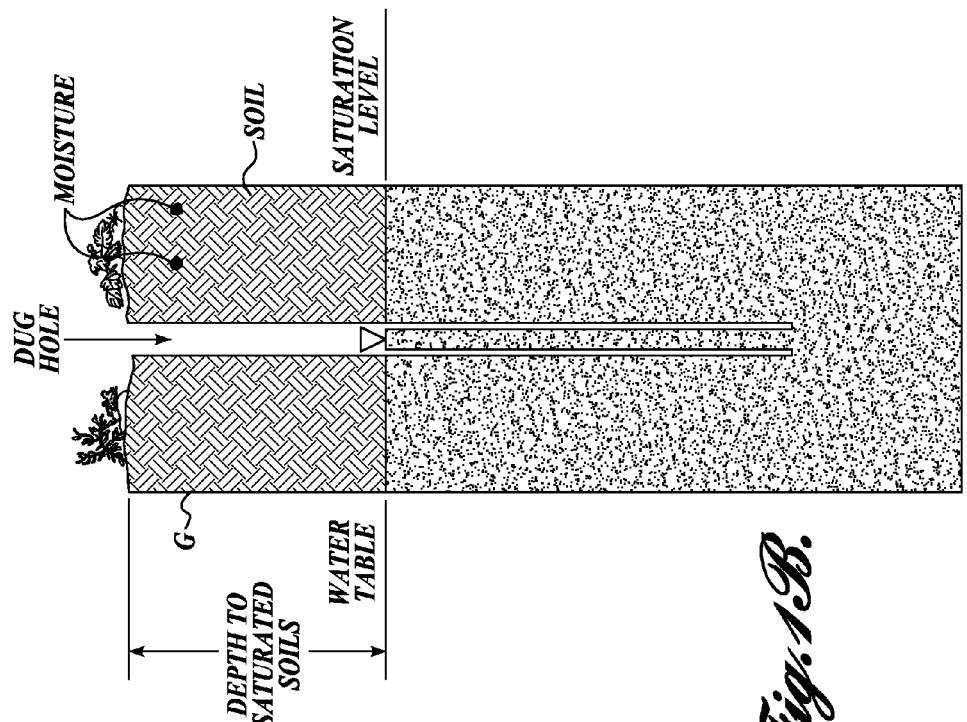
FIG. 1A is a cross-section of the ground that illustrates the capillary fringe in place, including the existence of top surface spans.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Referring initially to FIG. 2, illustrated is a system 100 for measuring the depth to saturated soil. The system 100 is shown installed in the ground G at a location of interest. The system 100, in basic form, includes a water level detector 102 alongside a stimulating device 104 which is capable of temporarily eliminating the capillary fringe adjacent the water level detector 102. Both the water level detector 102 and the stimulating device 104 are illustrated as disposed within a close fitting vertically elongate housing 106. The housing 106 is porous so as to enable groundwater to flow in and out of the housing. The housing may be constructed from non-rusting metal, plastic, or other suitable material. Also, the lower ends of the detector 102 and stimulating device 104 extend downwardly beyond the lower end of the housing 106. A. flange 108 extends transversely from the upper end portion of the housing to lie against the surface of the ground 109. In this manner, the flange 108 provides a reference level for the soil surface relative to the vertical elevations of the detector 102 and stimulating device 104. The flange 108 can completely encircle the housing 106 or partially encircle the housing 106.

The water level detector 102 is schematically illustrated in FIG. 2. The detector can be of various configurations, including in the form of a piezometer or a tensiometer. Both devices are able to measure the elevation of the groundwater relative to the elevation of the flange 108. Such piezometers and tensiometers are articles of commerce.

The stimulating device 104 is also schematically illustrated in FIG. 2. Although the device 104 is located within the housing 106, the device is positioned at least slightly away from the water level detector 102. The stimulating device 104 can take various forms. For example, in FIG. 2, the stimulating device is in the form of an upright tubular shape having perforations for taking in and expelling water. The water that flows into the stimulating device 104 may be from the surrounding groundwater.

To break down the pressure differential across the front at the saturation level, the stimulating device may be used to inject water at the level of or at an elevation below the level of saturation. In this regard, a small quantity of injected water is able to lift the sagging spans in front of the vicinity of the water level detector 102. For example, the amount of stimulating water may be as little as about 10 ml of water.

A pump 112 can be used to expel the water from the stimulating device 104 and into the ground below the level of saturation. The stimulating device 104 may be controllable or adjustable so that the water is injected into the ground at the correct elevation. The injection of the water into the ground at or near the capillary fringe rapidly and temporarily eliminates the capillary fringe pressure differential at the saturation level, causing the water table to rise to the saturation level.

Immediately after, or at least soon after the actuation of the stimulating device, the water level detector 102 is activated to measure the depth to saturated soil, i.e., the level of the water table relative to the elevation of flange 108.

It will be appreciated that if the activating fluid consists of the surrounding water that seeps into the stimulating device 104, then once the stimulating device has been activated to expel the collected water into the adjacent ground, a certain length of time is needed for the stimulating device to be recharged via an inflow of ground water.

Rather than relying on the inflow into the stimulating device of the surrounding ground water, water may be routed to the stimulating device from the water source 114. A valve 116 may be activated to control the flow of water into the stimulating device. Moreover, such water can be pumped into the stimulating device by pump 112, and the same pump used to force the water into the ground below the saturation level. Use of water from external reservoir source 114 allows use of the system 110 without having to wait until the stimulating device 104 is recharged from the surrounding ground water.

In situations where the stimulating water is from an external source, the stimulating device may have a different configuration than that shown in FIG. 2. The stimulating device can consist primarily of several branched lines that direct the water from the water source and into multiple locations within the capillary fringe or below the capillary fringe.

The operation of system 100 can be operated from the installation location of the system, for example, with a controller connected to the system. The system 100 can be programmed to periodically record the depth to saturated soil. On the other hand, it may be more convenient to control the operation of the system 100 remotely. In this regard, a remotely located control system 120 is shown in FIG. 4. The control system may include a processor 122 and a memory unit 124. An interface, such as a keypad 126, may be used to operate the control system. The control system may also utilize a display screen 128 useful for interfacing with the processor. Typically, communications between the control system 120 and the measuring system 100 will be conducted wirelessly via cell phone signals, radio frequency signals, microwave signals, or other wireless signals. To this end, an interface device 130 is provided for sending signals from, or receiving signals by, the control system 120. Receiver/transmitter units 132 and 134 are schematically illustrated with respect to system 100. A transmitter/receiver 126 is also schematically illustrated with respect to water valve 116. It will be appreciated that the control system 120 may control the operation of the system 100 as well as receive and record the water level data from the detector 102.

Figure 1B:
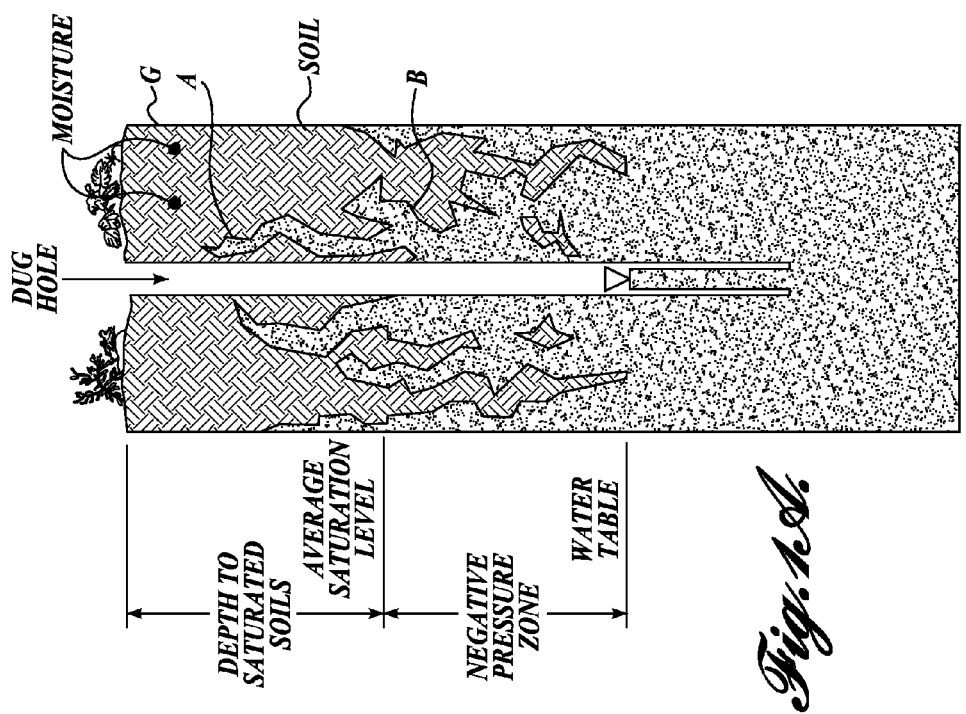
FIG. 1B illustrates the saturation level and water table when the capillary fringe is relaxed.

In the operation of system 100, when it is desired to measure the depth to saturated soil, the stimulating device 104 is actuated to inject a small quantity of water into the adjacent soil below the saturation level. This amount of water is capable of eliminating the capillary fringe consisting of a negative pressure that extends from the saturation level down to the water table. As a consequence, the top surface spans are relaxed so that the water table rises to the saturation level, as shown in FIG. 1B. At that time, the water level detector 102 is activated to measure the saturation level (water table). This information may be retained locally at the system 100 or transmitted to a remote location, for example, the location of controller 120. As will be appreciated, the system 100 enables measurement of the depth to saturated soil at desired intervals without the need for a technician, or other person, to be present at the measurement site.

The stimulating device 104 has been described as injecting a small amount of water into the adjacent ground below the level of saturation. However, other types of stimulating devices may be utilized; for example, the stimulating device may impart ultrasonic waves into the capillary fringe, which has the same effect as injecting water beneath the capillary fringe. In this regard, the stimulating device eliminates the pressure differential across the front at the saturation level.

As an alternative to use of an ultrasonic wave generator, the stimulating device may instead impart vibrations into the ground. Such vibrations typically could be from low to ultra high frequencies depending on soil conditions and other factors. Vibrations of these frequencies will also serve to eliminate the pressure differential across the front at the saturation level.

FIG. 3 illustrates a further embodiment of the present disclosure. FIG. 3 is similar to FIG. 2, but with the exception that a single stimulating device 104' is used in conjunction with two separate water level detectors 102'. Those components in FIG. 3 that correspond to the components in FIG. 2 are identified with the same part number, but with the prime "'" designation. As such, the construction and operation of the water level detectors 102' and stimulating device 104' will not be repeated here. Although two water level detectors 102' are shown in FIG. 3, a larger number of water detectors 102' may be utilized in conjunction with a singular stimulating device 104'. The operation of system 100' is the same as that of system 100, but rather than a singular depth to saturated soil level measurement being taken, two or more such measurements may be taken. Thus the system 100' has the advantage of being able to measure the depth to saturated soil at several locations adjacent the stimulating device 104'.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system for measuring a depth to saturated soil, comprising:
   (a) a water level detector capable of measuring a distance from the ground surface to a water table;
   (b) a stimulating device to direct an actuating medium into the ground at an elevation of a capillary fringe or below the elevation of the capillary fringe, thereby to temporarily eliminate the capillary fringe adjacent the water level detector; and
   (c) a recording device to record measurements of the water level detector of the distance from the ground surface to the water table.

2. The system according to claim 1, wherein the water level detector is selected from the group consisting of a piezometer and tensiometer.

3. The system according to claim 1, wherein the stimulating device for temporarily eliminating the capillary fringe comprising:
(a) a water receptacle positionable in the ground at an elevation corresponding to or below the elevation of the capillary fringe to receive water therein; and
(b) a pump to direct the water in the receptacle into the ground at an elevation corresponding to, or below, the capillary fringe.

4. The system according to claim 3, wherein the water receptacle is pervious to the groundwater to enable the groundwater to flow into and collect within the water receptacle.

5. The system according to claim 4, wherein the pump is in water flow communication with the groundwater that has collected in the water receptacle.

6. The system according to claim 3:
wherein the water receptacle is in water flow communication with a water storage container; and
further comprising a line to direct the water from the storage container to the water receptacle.

7. The system according to claim 1, wherein the stimulating device for temporarily eliminating the capillary fringe comprising:
a water source; and
a delivery system to route the water from the water source to beneath the ground surface and inject the water in the ground at the elevation of the capillary fringe or to the elevation below the elevation of the capillary fringe.

8. The system according to claim 7, wherein the delivery system comprising a. pump for injecting water from the water source into the ground at the elevation of the capillary fringe or into the ground at the elevation below the adjacent capillary fringe.

9. The system according to claim 1 wherein the stimulating device for temporarily eliminating the capillary fringe comprising a vibrator to impart vibratory energy into the ground at the location of the capillary fringe.

10. The system according to claim 9, wherein the vibrations are selected from the group consisting of ultrasound frequency emissions, and subsonic frequency vibrations.

11. The system according to claim 1, wherein the activating medium is selected from the group consisting of water, ultrasound frequency emissions, and vibrations.

12. The system according to claim 1, further comprising a control system for controlling the operation of the stimulating device to temporarily eliminate the capillary fringe as well as controlling the operation of the water level detector.

13. The system according to claim 12, wherein the control system further controlling the recording of the output from the water level detector.

14. A method for measuring a depth to saturated soil, comprising:
temporarily collapsing a capillary fringe by imparting an activating medium into the soil at or below an elevation of the capillary fringe; and
measuring the depth to saturated soil at the location of the collapsed capillary fringe immediately or very soon after the collapse of the capillary fringe.

15. The method according to claim 14, wherein the activating medium introduced into the soil comprises water in sufficient quantity to collapse the capillary fringe.

16. The method according to claim 15, wherein the water consists of collected groundwater.

17. The method according to claim 15, wherein the water is from a source remote from the location of the collapsed capillary fringe.

18. The method according to claim 14, wherein the depth to saturated soil is measured using an instrument selected from the group consisting of piezometers and tensiometers.

19. The method according to claim 14, wherein the activating medium introduced into the soil is selected from the group consisting of ultrasound waves as well as vibrations.

20. The method according to claim 14, further comprising transmitting the measurements of the depth to saturated soil to a remote location for monitoring and/or recording.

21. The method according to claim 14, further comprising sending control signals to initiate the temporary collapse of the capillary fringe and the subsequent measuring of the depth to saturated soil.

22. The method according to claim 21, wherein the control signals are transmitted from a controller located remotely from the site at which the depth to saturated soil is being measured.

* * * * *